United States Patent [19]

Mercado

[11] Patent Number: 4,777,041
[45] Date of Patent: Oct. 11, 1988

[54] WRINKLE TREATMENT FORMULATION

[75] Inventor: Clara Mercado, Aberdeen, N.J.

[73] Assignee: Charles of the Ritz Group Ltd., New York, N.Y.

[21] Appl. No.: 894,141

[22] Filed: Aug. 7, 1986

[51] Int. Cl.$^4$ .................................. A61K 31/74
[52] U.S. Cl. ............................ 424/78; 514/944; 514/844; 514/845
[58] Field of Search .............. 424/78, 47; 514/944, 514/844, 845

[56] References Cited

U.S. PATENT DOCUMENTS

| | | | |
|---|---|---|---|
| 3,822,238 | 7/1974 | Blair et al. | 260/75 |
| 4,304,591 | 12/1981 | Mueller et al. | 424/78 |
| 4,517,326 | 5/1985 | Cordts et al. | 424/78 |

FOREIGN PATENT DOCUMENTS 987301 3/1965 United Kingdom .............. 424/47

OTHER PUBLICATIONS

Husted, "Moisture Control in Aerosols", (1958).
*The Merck Index*, 10th ed. "Ethanol", Abst. 212 (1983).

*Primary Examiner*—Albert T. Meyers
*Assistant Examiner*—G. Krosnick

[57] ABSTRACT

A wrinkle treatment formulation is provided which is in the form of a gel formed of at least 95% by weight of a gelable hydrophilic polyurethane polymer base and a precipitated silica thickener gelling agent. Upon brushing the above-described gel formulation on wrinkled skin, the gel fills up wrinkles and dries to impart to so-treated skin a smooth substantially wrinkle-free appearance.

4 Claims, No Drawings

WRINKLE TREATMENT FORMULATION

FIELD OF THE INVENTION

The present invention relates to a wrinkle treatment composition which includes a hydrophilic polyurethane polymer base and a small amount of silica gelling agent.

BACKGROUND OF THE INVENTION

Until now, mass-marketed wrinkle treatment formulations have actually been moisturizer compositions in the form of creams, gels or lotions. Such compositions are applied to wrinkled skin and rubbed into wrinkled areas to produce a refreshing suppleness. However, they do not make wrinkles disappear or even mask same; wrinkles treated with such compositions are clearly visible.

DESCRIPTION OF THE INVENTION

In accordance with the present invention, a wrinkle treatment formulation is provided which when applied to wrinkled skin not only imparts a pleasant suppleness to it but also fills recessed areas forming the wrinkles so as to present a visibly smooth continuous surface. The wrinkle treatment formulation of the invention is formed of a gelable hydrophilic polyurethane polymer base which comprises at least about 95% by weight of such formulation, and a small gelling amount of silica gelling agent which comprises less than about 5% by weight of such formulation.

The gelable hydrophilic polyurethane polymer base will comprise the overwhelming major portion of the wrinkle treatment formulation of the invention and as such, will be present in an amount within the range of from about 95% to about 99.7% by weight of the formulation and preferably, from about 98.5% to about 99.5% by weight of the formulation and optimally, about 99.2% by weight of the formulation. The polymer base will be formed of a hydrophilic polyurethane polymer and an aqueous-alcoholic solvent therefor. The polyurethane polymer will comprise from about 3% to about 10% and preferably, from about 4% to about 8% by weight of the polymer base, and optimally, about 7% by weight of the polymer base, while the aqueous-alcoholic solvent will comprise from about 97% to about 90% by weight, and preferably from about 96% to about 92% by weight of the polymer base, and optimally, about 93% by weight of the polymer base.

The aqueous-alcoholic solvent will be preferably formed of ethanol employed on a weight ratio to water of within the range of from about 30:1 to about 10:1, and preferably from about 25:1 to about 15:1. Other alcohols may be employed in place of ethanol, such as isopropyl alcohol or isobutyl alcohol.

Hydrophilic polyurethane polymers which may be employed in the polymer base are fully described in U.S. Pat. No. 3,822,238 to Blair, et al. Examples of such hydrophilic polyurethane polymers suitable for use herein include, but are not limited to, a hydrammonium or quaternary ammonium salt of ethylene or propylene imine adducts of polyhydroxy compounds such as ethylene glycol, propylene glycol, glycerol, trimethylol propane, erythritol, pentaerythritol, anhydroenneaheptitol, sorbitol, mannitol, hydrolyzed low MW polyvinyl acetate, sucrose or lactose, which resin may contain an isocyanate such as tetramethylene diisocyanate, hexamethylene diisocyanate, trimethylhexamethylene diisocyanate, dimer acid diisocyanate, isophorone diisocyanate, hydrogenated diphenyl methane diisocyanate, methylene di(cyclohexyl isocyanate), metaxylylene diisocyanate, diethyl benzene diisocyanate, decamethylene 1,10-diisocyanate, cyclohexylene 1,2-diisocyanate, cyclohexylene 1,4-diisocyanate, 2,4- and 2,6-tolylene diisocyanate, 4,4'-diphenyl methane diisocyanate, dianisidine diisocyanate, tolidine diisocyanate, xenylene diisocyanate, 1,5-naphthalene diisocyanate and tetrahydro naphthalene-1,5-diisocyanate. However, other polymers as disclosed in U.S. Pat. No. 3,822,238 (the disclosure of which is incorporated herein by reference) may be employed herein as well.

The silica thickener-gelling agent will impart light reflectance to treated skin and further serves to tighten or cause treated skin to stretch and thereby hide wrinkles. It will be present in the wrinkle treatment formulation of the invention in an amount within the range of from about 0.3% to about 5%, preferably from about 0.5% to about 1.5%, and optimally about 0.8% by weight of the wrinkle treatment formulation. The preferred silica gelling agent is available as "HI-SIL T-690 Thickener" which is marketed by Silica Products and which has a surface area of from about 100 to about 200 meter$^2$/gram and preferably about 150 meter$^2$/gram and an average ultimate particle size of from about 10 to about 50 nanometers and preferably about 21 nanometers. The HI-SIL 600 silica will preferably have the following composition:

| Ingredient | % by Weight |
|---|---|
| SiO$_2$ anhydrous basis, % | 97.5 |
| Fe$_2$O$_3$, % | 0.1 |
| Al$_2$O$_3$, % | 0.5 |
| TiO$_2$, % | 0.007 |
| CaO, % | 0.3 |
| MgO, % | 0.1 |
| NaCl or Na$_2$SO$_4$ | 1.5 |

However, other known silica gelling agents may be employed such as precipitated or fumed silicas such as Syloid 72, Cab-O-Sil M5 or Aerosil 200.

Preferred wrinkle treatment formulations in accordance with the present invention are set out below:

| Ingredient | % of Weight |
|---|---|
| Hydrophilic polyurethane polymer base (polyurethanepolymer as described in U.S. Pat. No. 3,822,238) | 98.5 to 99.5 |
| Ethanol:water - 25:1 to 15:1 | 96 to 92 |
| Silica gelling agent | 0.5 to 1.5 |

To prepare the wrinkle treatment formulation of the invention, the silica gelling agent is mixed with the hydrophilic polyurethane polymer base and mixed together until the mixture is converted to a gel.

The gel may then be brushed onto wrinkled skin and allowed to dry. The dried gel fills up the recessed areas forming the wrinkles so that the treated skin gives the appearance of being smooth and uniform and free of wrinkles.

The dried gel may be easily washed away using soap and water.

The following Example represents a preferred embodiment of the invention.

EXAMPLE

A wrinkle treatment formulation in accordance with the present invention having the following composition was prepared as described below:

| Ingredient | | % by Weight |
|---|---|---|
| Polyurethane Polymer Base | | 99.2 |
| Polyurethane polymer (as described in Example 2 of U.S. Pat. No. 3,822,238) | 7% | base |
| Ethanol | 88% | |
| Water | 5% | |
| Silica gelling agent (HI-SIL-T-600) | | 0.8 |

The silica was added to the polymer base and the mixture was mixed with sweep mixing for 30 minutes until a clear-slightly hazy gel formed.

The gel was bottled in a nail-polish type container.

In use, the gel is simply brushed onto wrinkled skin and allowed to dry. Upon drying the gel fills up the wrinkles and thereby imparts to the skin a smooth appearance.

The gel is removed by washing the skin with soap and water.

What is claimed is:

1. A method for treating wrinkled skin which comprises applying to the skin a gel formulation comprising a gelable hydrophilic polyurethane polymer base present in an amount within the range of from about 95 to about 99.7% by weight and a silica gelling agent having a surface area of within the range of from about 100 to about 200 meters$^2$/gram present in an amount within the range of from about 0.3 to about 5% by weight, and allowing said gel formulation to dry on the skin to thereby fill up lined areas forming the wrinkles.

2. The method according to claim 1 wherein the polyurethane polymer base includes a solid polyurethane polymer and an aqueous alcoholic solvent therefore, the weight ratio of alcohol to water being within the range of from about 30:1 to about 10:1.

3. The method according to claim 1 wherein the silica gelling agent has an average particle size of about 21 nanometers.

4. The method according to claim 1 wherein the gel formulation comprises about 99.2% by weight polyurethane polymer base and about 0.8% by weight silica gelling agent.

* * * * *